United States Patent [19]

Wood et al.

[11] Patent Number: 4,941,454
[45] Date of Patent: Jul. 17, 1990

[54] SERVO ACTUATED STEERING MECHANISM FOR BORESCOPE OR ENDOSCOPE

[75] Inventors: Robert J. Wood; Earl H. Slee, both of Syracuse; Gregory E. Pasik, Auburn; Michael J. Pileski, Warners, all of N.Y.

[73] Assignee: Welch Allyn, Inc., Skaneateles Falls, N.Y.

[21] Appl. No.: 417,554

[22] Filed: Oct. 5, 1989

[51] Int. Cl.[5] .......................... A61B 1/00; G02B 7/00
[52] U.S. Cl. ........................................ 128/4; 356/241
[58] Field of Search ........................ 128/4, 6; 356/241

[56] References Cited

U.S. PATENT DOCUMENTS

| | | | |
|---|---|---|---|
| 4,253,447 | 3/1981 | Moore et al. | 128/6 |
| 4,261,344 | 4/1981 | Moore et al. | 128/6 |
| 4,294,233 | 10/1981 | Takahashi | 128/4 |
| 4,491,865 | 1/1985 | Danna et al. | 128/4 X |
| 4,559,928 | 12/1985 | Takayama | 128/6 |
| 4,621,618 | 11/1986 | Omagari | 128/6 |
| 4,659,195 | 4/1987 | D'Amelio et al. | 128/4 X |
| 4,688,555 | 8/1987 | Wardle | 128/4 |
| 4,787,369 | 11/1988 | Allred, III et al. | 128/4 |

Primary Examiner—William H. Grieb
Attorney, Agent, or Firm—Wall and Roehrig

[57] ABSTRACT

This invention involves a cable bendable borescope in which opposing cable pairs are displaced to deflect the tip of the borescope in the perpendicular planes of motion. A servo motor is connected to each pair of actuating cables to selectively displace one or the other in accordance with the rotation of the servo motor. A control circuit for rotating the servo motors has a pulse generation network and a modulator circuit for modulating the pulse width to control the degree of rotation of the servo motors. A joystick type of actuator for the control circuit creates a change in variable potentiometers for the two directions of motion of the joystick which, in turn, causes the control circuit to rotate the servo motors for the corresponding plane of motion to produce the desired deflection of the tip of the borescope insertion tube. Tension control, centering and component compensation circuits are provided to limit stress on the cables. The servo motors are slidably mounted on a track with spring anchors to the frame chosen to allow the entire assembly to move to limit tension in the actuating cables to a predetermined amount.

11 Claims, 3 Drawing Sheets

SERVO ACTUATED STEERING MECHANISM FOR BORESCOPE OR ENDOSCOPE

BACKGROUND OF THE INVENTION

This invention relates generally to a borescope or endoscope for providing full color video images of inaccessible objects of the type having a cable actuated steering section, and more particularly to a compact portable battery operated borescope having a servo motor controlled steering section.

A borescope is generally characterized as an elongated flexible insertion tube with a viewing head at its distal end and a control and processing section at its proximal end. The control section has generally included one or two pairs of control cables extending from the bendable tube section through the remainder of the insertion tube to connect with the steering control mechanism in the control section. These steering mechanisms typically have involved a rack and pinion steering mechanism with large control knobs for manipulation of the steering in two planes disposed ninety degrees to each other. One or both pairs of these cables are differentially displaced for bending the steering section to facilitate the inspection of an object. Various devices have been provided in the prior art for realizing a full color video picture of a target situated within a remote cavity. These devices have been gradually improved over time to where today, most devices of this type employ an external light source conveyed to the image viewing head by fiber optic bundles, together with a solid state image sensor and lens system positioned in the distal end of the insertion tube of the borescope connected to an external video processing system and standard television format display equipment.

Endoscope/borescope systems of this general type have been disclosed in various patents owned by a common assignee of the present applicant, such as Moore et al. U.S. Pat. No. 4,253,447; Moore et al. U.S. Pat. No. 4,261,344; and Danna et al. U.S. Pat. No. 4,491,865. Another endoscope system is shown in Omagari U.S. Pat. No. 4,621,618, which describes a central control/display/light station, and a drive motor body for the insertable endoscope portion. The central control has a joystick actuated motor drive circuit for a motor mounted adjacent to and which manipulates the wire controlled bendable section of the insertion tube. This rather large cumbersome system requires a paramedic to handle the endoscope while the doctor operates the device from the control station. Also, the apparatus obviously is not portable.

As part of the need for greater flexibility and portability, the control of the steering function of a borescope has had to be simplified and improved both from an operating and from an adjustability and maintenance viewpoint. Not only is it important to be able to operate a compact portable system by a single person from a variety of locations relative to the main processing module, but the requirement for the precise positioning and for very tortuous access in industrial products has greatly increased the demand for maintaining the instruments in optimum steering adjustment at all times.

As is well known in the art, frequent use or abuse of a cable actuated bending section of a borescope will stretch the cables to the point that steering accuracy is lost and precise positioning is impossible. One of the major problems faced by the industry is the constant need to readjust and refurbish the steerable insertion tube portions of borescope apparatus. A great deal of time and money is invested constantly by users of these systems to repair and readjust bendable insertion tubes in which the cables have been stretched or broken.

OBJECTS AND SUMMARY OF THE INVENTION

It is therefore an object of the present invention to provide a steering system for a cable actuated bendable tube borescope assembly that avoids the drawbacks of the prior art.

It is another object of the present invention to provide a steering control for a cable actuated bendable tube borescope that can be easily actuated with one hand.

It is another object of the present invention to provide a control system for a cable actuated bendable tube borescope that can be readily adjusted for cable stretch in the field without complicated and costly factory readjustment.

It is another object of the present invention to provide a borescope steering control that is power actuated and automatically adjusts cable tension to minimize cable stretch.

It is a still further object of the present invention to provide a borescope steering control with a large number of field adjustments for optimizing cable tension to obtain accurate and precisely controlled bending.

It is a further object of the present invention to provide a field adjustable calibration mechanism for setting up in the field a cable actuated bendable tube borescope.

It is a further object of the present invention to provide a servo motor control circuit for precisely rotating a servo motor the desired amount that allows the operator to precisely position the viewing head of the borescope using minimum power consumption.

It is a still further object of the present invention to provide a pulse generating network for driving the servo motor control of a bendable tube borescope in which pulse width may be varied to precisely control the degree of rotation of the servo motor.

It is a still further object of the present invention to provide means for electrically adjusting the tension applied to the steering cables of a bendable tube borescope that will obviate the need for complicated and difficult mechanical adjustments.

These and other and further objects and features of the invention will be more fully understood from the ensuing detailed description of the preferred embodiments of the invention which description should be read in conjunction with the accompanying drawings.

DETAILED DESCRIPTION OF THE PREFERRED EMBODIMENT

Figure 1:
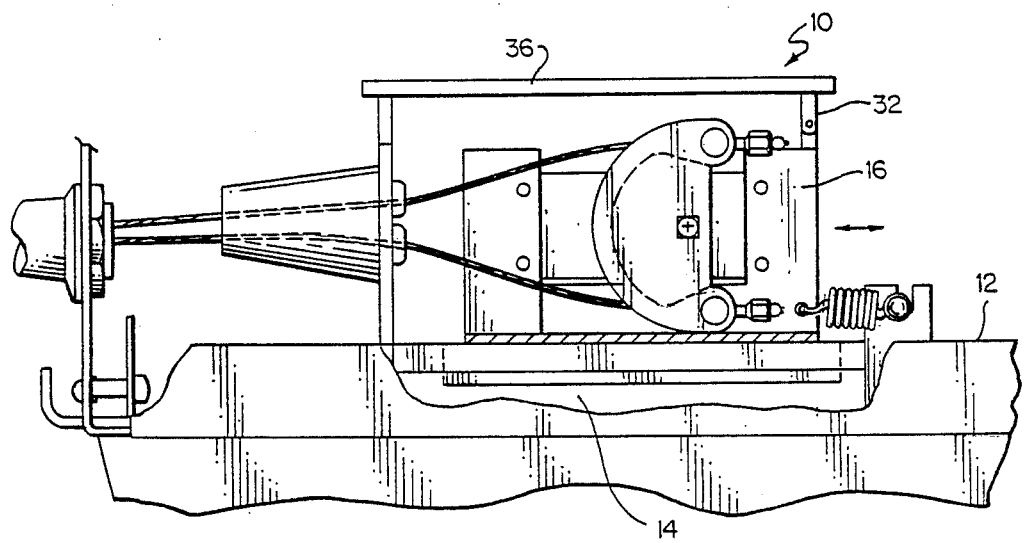
FIG. 1 is a side elevation partially broken away of a servo control according to the present invention.
Figures 2, 4:
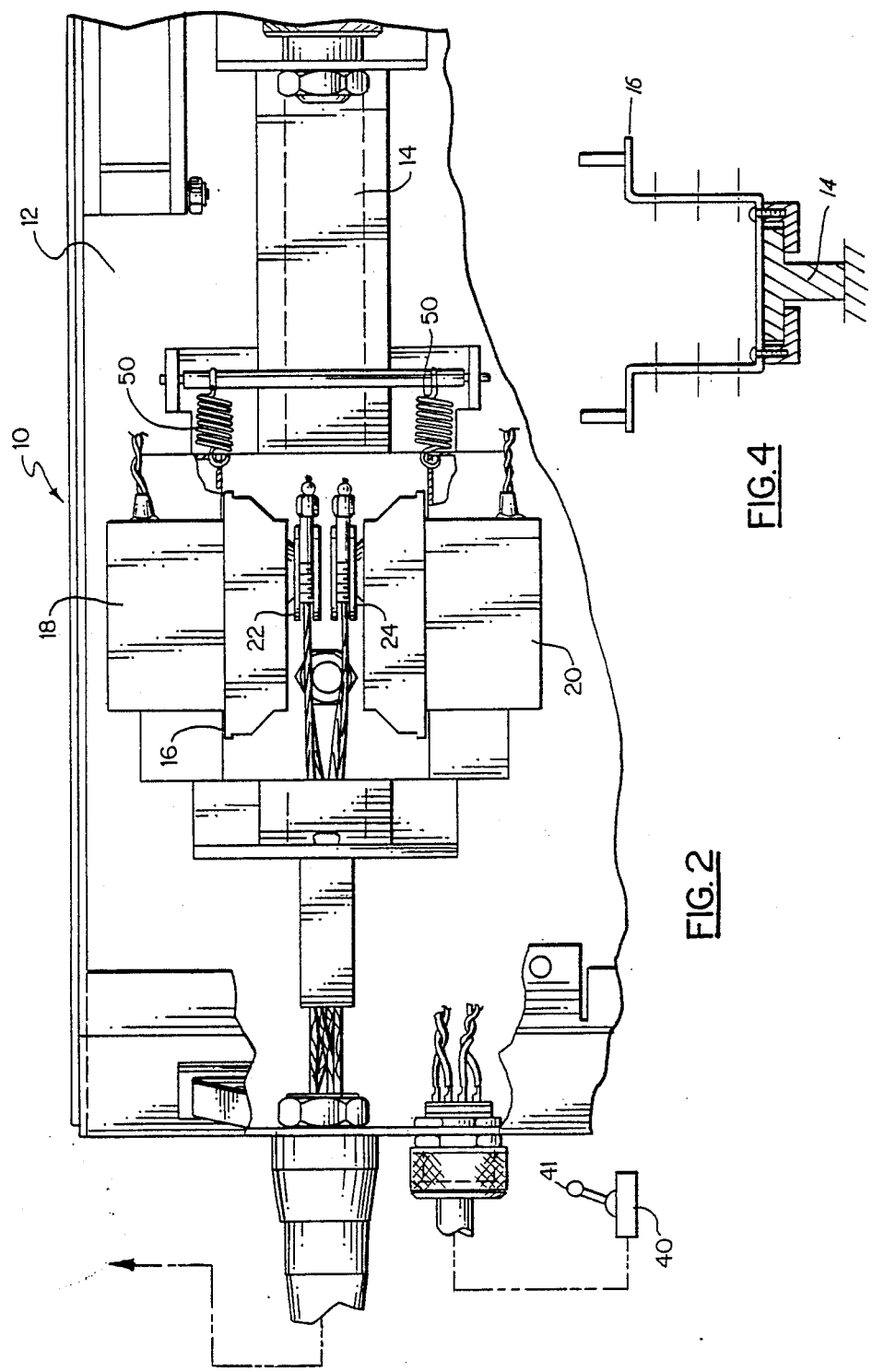
FIG. 2 is a top plan view of the device of FIG. 1.
FIG. 4 is a cross sectional view of the track and mounting platform of the servo motor control of the present invention.

Referring now to FIG. 1, there is shown a servo control articulation system 10 for a borescope. The chassis of the control module is shown at 12 and the chassis carries therein a T-shaped mounting rail 14 on which is slidably mounted a U-shaped bracket 16 (FIG. 4). Plate 16 carries thereon the servo motors 18 and 20 (FIG. 2), each of which has mounted on its output shaft semi-circular quadrants 22 and 24. Mounted at the opposite ends of the diameter of the semi-circular quadrant 24 on motor 20 are cable retaining ferrules 26 and 28 (FIG. 5) to which are connected the wires 30 and 32 for actuating the bendable tube section of the borescope insertion tube in one direction. The other servo motor 18 carries on its quadrant 22 a similar pair of adjustable cable ferrules 26' and 28' which are connected to the second pair of actuating wires 30' and 32' for controlling the insertion tube distal end in a plane at ninety degrees to the plane of motion of the first pair. The connection of two pair of wires at right angles to each other at the distal end of an insertion tube is common and shown in the references previously cited.

Pivotally mounted by the hinges 32 directly above the servo motors is a steering control board 36 which carries thereon a pulse generating circuit and a pulse width modulator section 62, together with a centering section 64 and a gain and offset section 66 for matching a joystick type actuator 40 to the servo motors 18 and 20 and limiting rotation thereof. The details of the control circuit will be described in connection with FIG. 3.

As may be seen in FIGS. 1 and 2, the servo motors are mounted on bracket 16 which is slidably mounted on the T-bar 14 (FIG. 4). The cables 30–32 and 30'–32', which extend out through the insertion tube to the bendable section at the distal end, are connected physically to the quadrants 22 and 24 at the opposite ends of a diameter as described above. In operation, as the servo motor is rotated under control of the joystick, and its associated circuitry, one cable will be tensioned to bend the insertion tube in that direction and the opposite cable of the pair will have the tension removed so that it can move with the tube end as it bends. As will be described herein, the degree of rotation is controlled by the various electrical settings so that the device may be set up and calibrated and the tension applied to the wires controlled. The modulator 62 includes an oscillator which generates pulses at the desired frequency and circuitry to vary the pulse width in accordance with the voltage applied at the inputs 63 and 63' of the pulse width modulator. Typical pulse widths for the oscillator pulse may vary from 1.0 milliseconds to 2.0 milliseconds.

If during actuation an obstacle is encountered at the end of the insertion tube, or if for some other reason, such as friction from coiling of the insertion tube, the tension in the wire tends to exceed the desired amount, it will pull on its servo motor which is fixed to the bracket 16 mounted on the track 14. The bracket 16 is connected to the chassis by a pair of springs 50 which are selected to yield above a given predetermined tension or force applied thereto. Thus, if the tension in the wire or cable exceeds the desired predetermined amount, instead of stretching the wires, the entire servo assembly will move toward the insertion tube or to the left in FIG. 1 and thus prevent the tension in the wires exceeding the predetermined amount.

Since both servo motors are mounted on the same plate, excess tension in either pair of wires will move the entire assembly and will tend to relieve tension on both pairs of wires. Generally speaking, if excess tension is being encountered in one pair, the other pair will also be subjected to excessive tension so that the two springs are sized to prevent excessive tension in either or both pairs.

The servo motors 18 and 20 are actuated by applying a pulse, typically five volts, of a desired width which represents a particular angular position of the quadrant 22 and 24. The pulses are applied at any desired frequency, for instance sixty hertz, and as long as the pulse width remains constant the servo motors remain stationary.

A predetermined pulse width is chosen that will maintain the steerable section of the insertion tube in the straight position when the joystick control is in the neutral position and then the pulse width is decreased or increased proportional to the movement of the joystick actuator 41 to bend the distal end of the insertion tube the desired amount.

Rotation of the servo motors is accomplished by applying the voltage pulses to the motors. The degree of rotation is controlled by varying the width of the pulses applied to the servo motors through the modulator 62.

Figure 3:
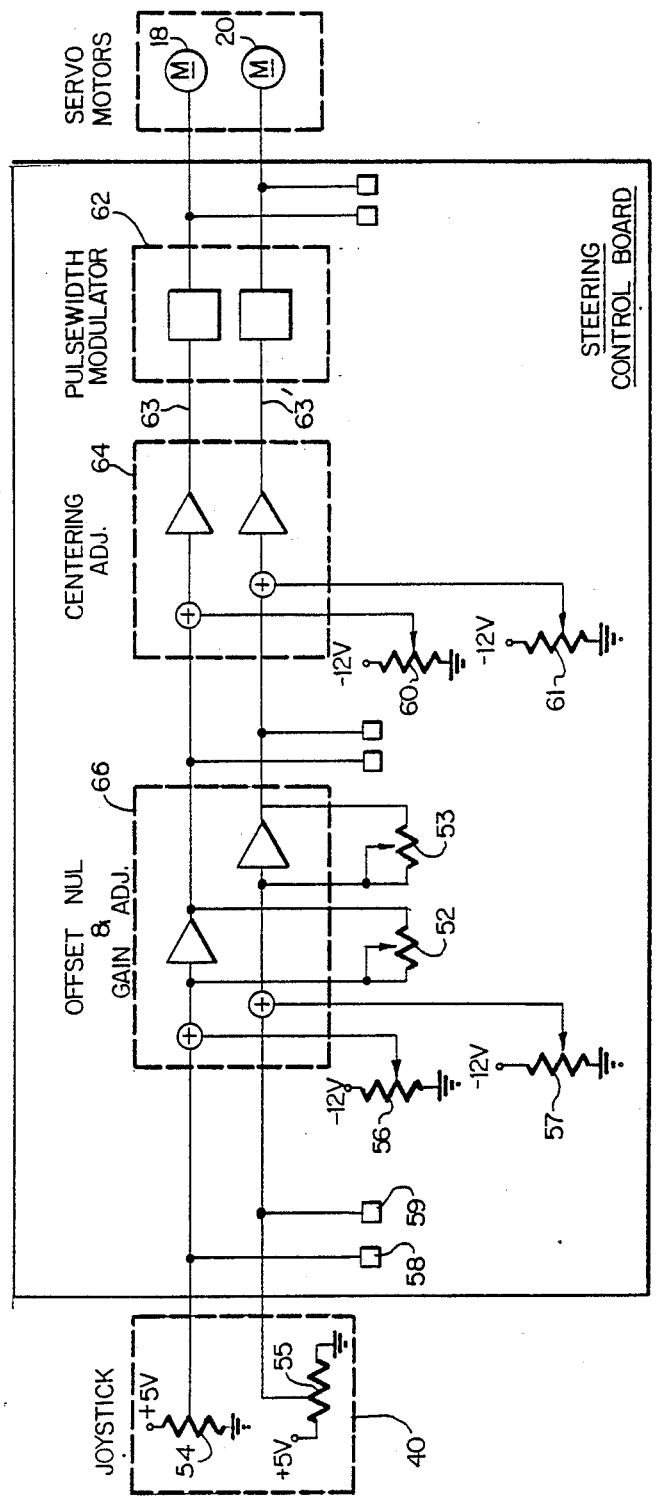
FIG. 3 is a schematic block diagram of a control system for the present invention.

The gain adjustment section of the steering control board in FIG. 3 determines the maximum range of pulse widths that can be created by the modulator 62 and hence the maximum rotation of the quadrants. Potentiometers 52 and 53 are originally set to permit rotation of about plus or minus sixty-five degrees maximum.

The amount of tension that can be applied by the servo motors is determined in part by the original adjustment of the cable retaining ferrules 26 and 28 and then by the maximum degree of rotation of the quadrant. The degree of rotation of the quadrants 22 and 24 is determined by the amount of displacement of the joystick and by the position of potentiometers 52 and 53 in FIG. 3. This adjustment can be changed to compensate for stretch in the wires over time by allowing the servo to rotate further and to thus still maintain the tension in the wire for maximum bending of the bendable distal end of the borescope insertion tube.

If by chance the limits of adjustment of the potentiometers 52 and 53 are exceeded, the ferrules 26 and 28 can be mechanically tightened to take up slack and then the potentiometers readjusted to provide the desired tension.

This potentiometer adjustment is a simple screwdriver adjustment on the board 36 which can be readily done in the field without sophisticated instruments. This saves many costly and time consuming returns of the insertion tube to the factory for refurbishing and readjustment. Since the springs are set so that the tension on the wires will not exceed their elastic limit, excessive stretching of the wires is prevented, and only a slight stretching over time is encountered, which can normally be completely compensated for by the foregoing means.

It will be understood that as the servo motor is actuated, it will rotate plus or minus forty-five to ninety degrees, and as such the respective wires of the top and bottom of FIG. 1 will be wrapped around the quadrant through the channel 42 by the appropriate degree of rotation of the quadrant.

Figure 5:
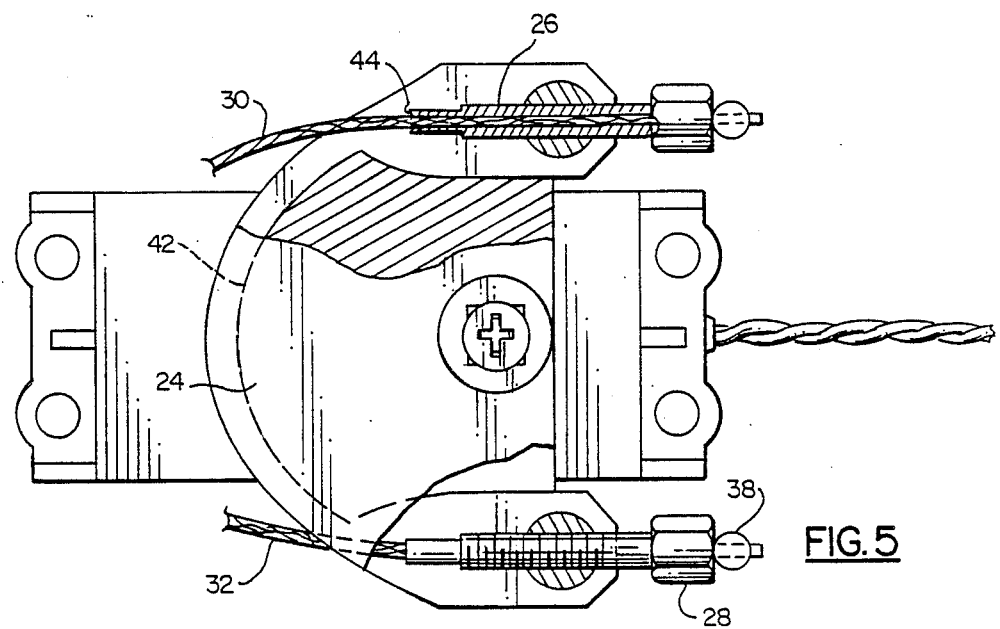
FIG. 5 is a detailed view of the servo quadrant and cable attachment detail of the present invention.

As may be seen in FIG. 5, the ferrules 26 and 28 are threadably mounted in the periphery of the quadrant 24 and carry therethrough the wires 30 and 32 with a termination that can either be crimped or soldered in the form of a ball 38 to secure the wire within the ferrule. The ferrules 26 and 28 can then be adjusted to tension the wires 30 and 32 sufficiently to position the bendable section of the borescope insertion tube at center position in the corresponding plane for wires 30 and 32. The ferrules 26' and 28' can similarly be adjusted for wires 30' and 32'. It should be noted that each ferrule is mounted in a slight recess in the quadrant such that the wire, as it exits the ferrule, makes a smooth transition into the channel 42 in the periphery of the quadrant such that when the quadrant is rotated from the center position, the wire will not be cut by the quadrant as it exits the ferrule. The ferrule also has a chamfer 44 to enhance this smooth transition.

Referring now to FIG. 3 there is shown, in block diagram form with the adjustments shown in schematic form, the circuitry for controlling and adjusting the pulse width drive for the servo motors 18 and 20. The modulator 62 includes an oscillator which generates pulses at the desired frequency and circuitry to vary the pulse width in accordance with the voltage applied at the input 63 and 63' of the pulse width modulator. The joystick control 40 consists basically of two potentiometers 54 and 55, one actuated by the "x" direction of motion of the joystick 41 and the other actuated by the "y" direction of motion of the joystick 41. As may be seen in FIG. 3, a positive five volt power source is connected to resistors 54 and 55 with the other side of each potentiometer connected to ground. Since this joystick lever 41 is spring biased to a neutral position, calibration compensation potentiometers 56 and 57 are provided to compensate for any slight misalignment there may be in the mechanical construction of the joystick. Each potentiometer 56 and 57 is connected from a −12 volt power supply to ground, and they are adjusted to yield zero voltage at the test points 58 and 59 on initial set up and calibration. Just as the joystick has a built-in center position, which must be compensated for, the servo motors 18 and 20 have built-in variations that must be compensated for to obtain the desired zero bending in the neutral position.

Accordingly, a centering adjustment is provided by another pair of potentiometers 60 and 61, connected between −12 volts and ground. With the joystick 41 in neutral, the potentiometers 60 and 61 are adjusted to provide an input voltage at 63 and 63' to pulse width modulator 62, corresponding to the zero bending of the distal end of the insertion tube while also compensating for any anomalies in the servo motors themselves. Typically, the neutral pulse width is set at 1.5 milliseconds, which allows plus or minus variation from 1.0 milliseconds to 2.0 milliseconds pulse widths.

Variations of the voltage at 63 and 63' will cause the pulse width produced by modulator 62 to increase or decrease which will in turn cause servo motors 18 and 20 to rotate in a clockwise or counterclockwise direction from the center neutral position to actuate the bendable distal end of the insertion tube in the desired direction.

As indicated above, the modulator 62 provides a series of pulses at a frequency of typically sixty hertz, which vary in width as the lever 41 is moved, creating an offsetting voltage from the neutral position, proportional to the amount of movement of the lever. This voltage is fed from joystick control 40 through the Offset Null adjustments 56 and 57 and Maximum Gain adjustments 52 and 53 and centering adjustment potentiometers 60 and 61 which drive the respective channels in the modulator to either increase or decrease the width of the pulses. The greater the variation from the neutral voltage at 63 and 63' either plus or minus, the greater the degree of rotation of the servo motors from the neutral position.

In operation the device is adjusted so that the joystick and the servo motors are "zeroed out" in the neutral position to provide zero bending of the steerable section of the insertion tube. The normal maximum deflection of the servo motors may be adjusted by potentiometers 52 and 53, for instance, to plus or minus forty-five degrees in each direction for the original cables which, in the unobstructed and uncoiled condition, will actuate the steerable portion of the insertion tube to its maximum bending in each plane of motion. As described above, as the cables 30 and 32 stretch, the particular servo motor actuating these cables may be adjusted to rotate plus or minus a greater amount, up to ninety to one-hundred degrees at the extreme, which is effectuated by changing potentiometers 52 and 53 to provide greater pulse width out of the pulse width modulator 62 so as to cause the greater rotation of the servo motor. Since this is now a simple screwdriver adjustment of a potentiometer, it can be easily done by field operating personnel and thus the insertion tube control can be kept in optimum condition without having to return it to the factory for calibration and adjustment.

It should be noted that the tension of cables 30 and 32 or cables 30' and 32' can be independently adjusted by their respective potentiometers 52 or 53 for optimum actuation control.

With the joystick controlling the servo motors, the operator of the borescope can now, with one hand, direct the insertion tube to the precise location desired by monitoring the image on the tv screen and actuating the bendable tip to move in the direction it is desired to go as the insertion tube is inserted into the cavity to be inspected. As described herein, the operator cannot damage the insertion tube control system because if he hits an obstruction or if he exceeds the predetermined tension of the actuation cables, the entire servo control mechanism will be moved along the T track 14 against the springs 50, which are chosen to yield before the actuating cables are stretched.

There is thus provided a very simple, rugged, easily adjusted and largely self-compensating actuation system for a cable actuated bendable borescope insertion tube.

While this invention has been explained with reference to the structure disclosed herein, it is not confined to the details as set forth and this application is intended to cover any modifications and changes as may come within the scope of the following claims.

What is claimed is:

1. In a steerable endoscope/borescope of the type having an elongated insertion tube with a viewing head at the distal end, a cable bendable articulation section proximally of the viewing head, and at least one pair of steering cables operatively connected to said articulation section, articulation control means comprising:
    a servo motor connected to each said pair of cables,
    steering control means connected to said servo motor, actuator means connected to said steering control means including at least one variable voltage means operatively connected to increase or decrease in value as said actuator is moved in one direction of motion, said steering control means including a pulse generating network and a pulse width modulator circuit for varying the width of generated pulses in accordance with changes in said variable voltage means;

said variations and pulse width causing said servo motor to rotate a predetermined number of degrees corresponding to the position of said actuator means, so that the bendable section of the insertion tube is actuated the desired amount.

2. A device as described in claim 1 further defined by said steering control means including potentiometer means for limiting the width of the pulse applied to the servo motor so that servo rotation cannot exceed a predetermined limit.

3. A device as described in claim 2 further characterized by second potentiometer means for centering the position of the servo motor, with the joystick in the neutral position, to correspond with the straight position of the bendable distal end of the insertion tube.

4. A device as described in claim 3 further defined by third potentiometer means for compensating for the manufacturing tolerances in the joystick neutral position to allow calibration of the servo motor control system to a particular joystick control.

5. A device as described in claim 1 wherein said pulse generating network produces pulses at the rate of sixty per second and said pulse modulator varies the width of the individual pulses from a duration of 1.0 milliseconds to 2.0 milliseconds so as to rotate said servo motor the desired number of degrees.

6. A device as described in claim 1 wherein said steering control means includes voltage control means connected in each servo motor control network for independently adjusting the pulse width limits of the pulses applied to the respective servo motor so that stretching of each pair of bending cables can be individually compensated for by a field electrical adjustment.

7. In a steerable borescope/endoscope of the type having a cable bendable steering section at the distal end of an insertion tube, a cable actuation and tension control means comprising:

a frame member;

a mounting plate slidably mounted on a track fixed on said frame member;

at least one servo motor mounted on said plate;

lever means mounted on the output shaft of said servo motor;

a pair of bending cables connected to said lever means at opposite ends thereof;

steering control means operatively connected to said servo motor for rotating said lever means a selected number of degrees, spring means connected between said frame member and said mounting plate so that when tension in a cable exceeds a preset value, said mounting plate will slide on the track and said springs will be extended to limit said excess tension, actuator means for converting a mechanical motion to an electrical signal;

said actuator means being electrically connected to said steering control means so that movement of said actuator means will cause a corresponding bending of said distal end of the insertion tube without stretching said bending cables.

8. A device as described in claim 7 further defined by said bending cables being connected to said lever means by a threaded ferrule rotatably mounted thereon so that they can be extended or retracted to increase or decrease tension in the actuating cable.

9. A device as described in claim 8 further characterized by said lever means consisting of a semi-circular quadrant member having a wire receiving channel about the periphery thereof, and by said threaded ferrule being mounted in a recess on the periphery of said quadrant so as to provide a smooth transition for the cable from the ferrule to the channel in the periphery of the quadrant so as to prevent cutting of the cable upon rotation of the quadrant.

10. A device as described in claim 7 wherein said steering control means includes a pulse generating network, circuit means for modulating the width of said generated pulses in accordance with the position of said actuator means and variable potentiometer means for limiting the rotation of said servo motor to prevent unwanted stretching of the steering cables.

11. A device as described in claim 7 further defined by said actuator means being a self-contained joystick remotely positioned from said steering control means and connected thereto by flexible electrical wire.

* * * * *